United States Patent [19]

Ramig et al.

[11] Patent Number: 5,420,305
[45] Date of Patent: May 30, 1995

[54] PROCESS FOR THE PREPARATION OF (R)-3-HEXYL-5,6-DIHYDRO-4-HYDROXY-6-UNDECYL-2H-PYRAN-2-ONE AND (R)-5,6-DIHYDRO-6-UNDECYL-2H-PYRAN-2,4 (3H)-DIONE

[75] Inventors: Keith M. Ramig, Orange, N.J.; John J. Landi, Jr., East Stroudsburg, Pa.

[73] Assignee: Hoffmann-La Roche Inc., Nutley, N.J.

[21] Appl. No.: 131,843

[22] Filed: Oct. 4, 1993

Related U.S. Application Data

[60] Division of Ser. No. 849,908, Mar. 12, 1992, Pat. No. 5,274,143, which is a continuation-in-part of Ser. No. 734,408, Jul. 23, 1991, abandoned.

[51] Int. Cl.⁶ .............................. C07D 309/32
[52] U.S. Cl. ............................ 549/292; 549/294
[58] Field of Search ........................ 549/292, 294

[56] References Cited

U.S. PATENT DOCUMENTS

| | | | |
|---|---|---|---|
| 2,542,849 | 10/1948 | Glahn et al. | 549/292 |
| 4,206,222 | 6/1980 | Valetas | 549/292 |
| 5,245,056 | 9/1993 | Karpf et al. | 549/510 |

*Primary Examiner*—C. Warren Ivy
*Assistant Examiner*—Ba K. Trinh
*Attorney, Agent, or Firm*—George M. Gould; George W. Johnston; Ellen Ciambrone Coletti

[57] ABSTRACT

A process for the preparation of a tautomeric mixture of compounds of the formulas

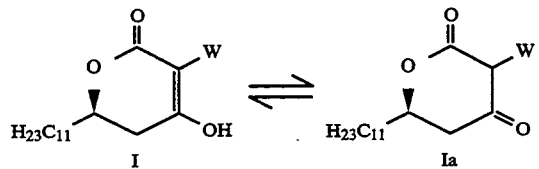

wherein W is hydrogen or $C_6H_{13}$, which comprises treating a compound of the formula

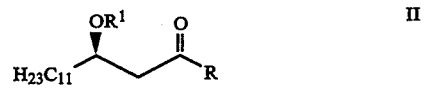

wherein R is unsubstituted or substituted alkoxy, arylalkoxy, aryloxy or amine and $R^1$ is hydrogen or when R is alkoxy, substituted alkoxy, substituted amine, unsubstituted or substituted arylalkoxy $R^1$ can also be metal, with a compound of the formula

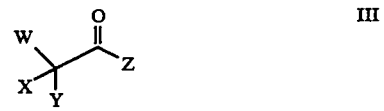

wherein W is as described above, both X and Y are reducible groups or X is hydrogen and Y is a reducible group or Y is hydrogen and X is a reducible group and, Z is hydroxy or a leaving group to form the compound of formula IV

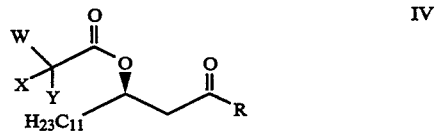

wherein W, X, Y and R are as defined above, the compound of formula IV is treated with a low valent metal to form a tautomeric mixture of compounds of formulas I and Ia, which are useful in the synthesis of tetrahydrolipstatin.

16 Claims, No Drawings

PROCESS FOR THE PREPARATION OF (R)-3-HEXYL-5,6-DIHYDRO-4-HYDROXY-6-UNDECYL-2H-PYRAN-2-ONE AND (R)-5,6-DIHYDRO-6-UNDECYL-2H-PYRAN-2,4 (3H)-DIONE

This is a division of U.S. Pat. application Ser. No. 07/849,908 filed Mar. 12, 1992 now U.S. Pat. No. 5,274,143, which is a Continuation-in-part of Ser. No. 07/734,408, filed Jul. 23, 1991, now abandoned.

BACKGROUND OF THE INVENTION (R)-3-hexyl-5,6-dihydro-4-hydroxy-6-undecyl-2H-pyran-2-one and (R)-5,6-dihydro-6-undecyl-2H-pyran-2,4(3H)-dione are known precursors for the preparation of tetrahydrolipstatin, which exist in tautomeric form.

The known methods of preparing (R)-3-hexyl-5,6-dihydro-4-hydroxy-6-undecyl-2H-pyran-2-one, include that set forth in Barbier, et al., J.Org. Chem., Vol. 53,pgs. 1218–1221 (1988). In particular, that process comprises a multiple step process described in reaction scheme I below:

SCHEME I

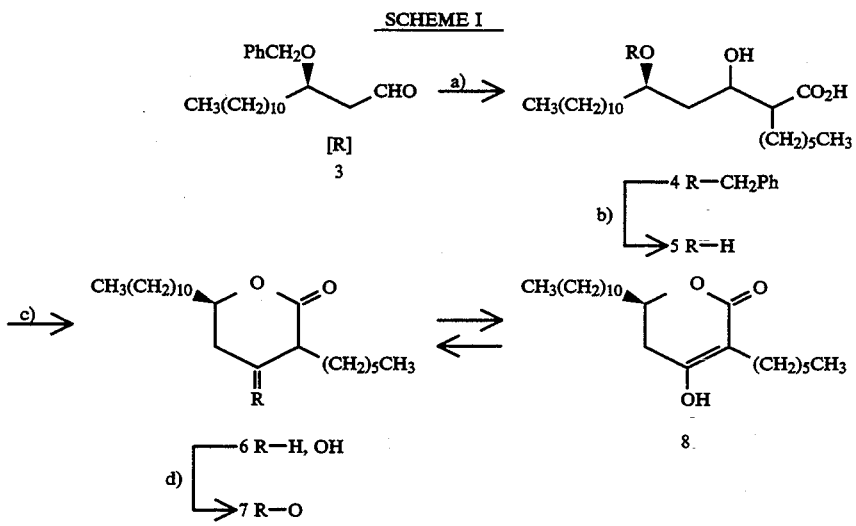

(a) Octanoic acid, LDA;
(b) $H_2$, Pd/C, 10%;
(c) p-TsOH, CHCl$_3$;
Jones' oxidation;

A method for the preparation of (R)-5,6-dihydro-6-undecyl-2H-pyran-2,4(3H)-dione includes that set forth in co-pending U.S. application Ser. No. 07/653,846, filed Feb. 11, 1991. In particular, that process comprises hydrogenolyzing and cyclizing a compound of the formula:

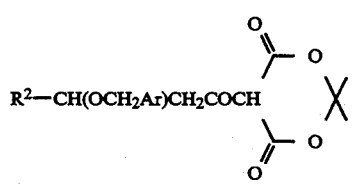

wherein $R^2$ is $C_{11}H_{23}$; Ar is phenyl substituted by 1 to 3 groups $R^9$ or $OR^9$ wherein $R^9$ is hydrogen or $C_{1-3}$ alkyl.

BRIEF SUMMARY OF THE INVENTION

The invention relates to a process for the preparation of a tautomeric mixture of compounds of the formulas

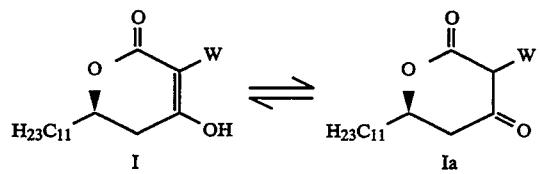

wherein W is hydrogen or $C_6H_{13}$, which comprises treating the compound of the formula

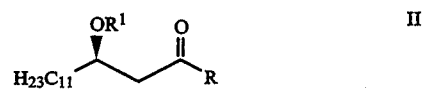

wherein R is unsubstituted or substituted alkoxy, aryl alkoxy, aryloxy or amine; $R^1$ is hydrogen or when R is alkoxy, substituted alkoxy, substituted amine, unsubstituted or substituted arylalkoxy, $R^1$ can also be metal, with the compound of the formula III

wherein both X and Y are reducible groups or X is hydrogen and Y is a reducible group or Y is hydrogen and X is a reducible group; W is hydrogen or $C_6H_{13}$, and Z is hydroxy or a leaving group, to form a compound of formula IV

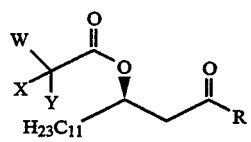

wherein R, X and Y are as defined above and W is hydrogen or $C_6H_{13}$, the compound of formula IV is treated with a low valent metal to form a tautomeric mixture of compounds of formulas I and Ia.

The compounds of formulas I and Ia are known precursors for the preparation of tetrahydrolipstatin and thus are useful in the synthesis of tetrahydrolipstatin, see, for example, Barbier, et al., J. Org. Chem. Vol. 53, pgs. 1218–1221 (1988), and copending U.S. application Ser. No. 07/653,846.

DETAILED DESCRIPTION OF THE INVENTION

In the formulas represented herein, when substituents are illustrated as joined to the nucleus by a solid line (━━), it indicates that the substituent is in the β-orientation, that is, above the plane of the molecule, a broken line (⋯⋯), indicates that the substituent is in the α-orientation, that is, below the plane of the molecule.

As used herein, the term "leaving group" denotes a group subject to nucleophilic substitution, such as, for example, halogen, preferably chlorine; unsubstituted or substituted alkoxy, other than tert butyloxy and tert amyloxy, preferably methoxy; unsubstituted or substituted aryloxy, unsubstituted or substituted acyloxy, alkoxy carbonyloxy and amino carbonyloxy.

The term "reducible group" denotes a group subject to reductive removal by low valent metals, such as, for example, halogen, preferably bromine; alkylsulfide, arylsulfide, alkylselenide, arylselenide and the like.

The term "alkyl", alone or in combination, denotes a straight-chain or branched chain alkyl group containing 1 to 7, preferably 1 to 4, carbon atoms, especially preferred is methyl. The term "alkoxy", alone or in combination, denotes an alkyl group as defined earlier which is attached via an oxygen atom, examples of alkoxy groups are methoxy, ethoxy, propoxy, isopropoxy, butoxy, and the like.

The term "aryl", alone or in combination, denotes a monocyclic or polycyclic aromatic group, preferably a monocyclic or bicyclic group, for example, phenyl or naphthyl. Exemplary of aryl in combination with alkyl denotes, for example, benzyl.

The term "acyloxy", alone or in combination denotes alkyl or aryl attached to a carboxyl group, such as, for example, acetoxy, benzoyloxy and the like.

The term "substituted alkoxy" denotes an alkoxy group, as defined earlier, which is substituted with, for example, one or more substituents selected from alkoxy, alkoxyalkoxy, dialkylamino alkoxy, fluorine, and aryl.

The term "substituted aryloxy" denotes an aryloxy group as defined earlier which is substituted with one or more substituents, for example, substituents selected from 2-nitro, 4-nitro, 2-alkoxycarbonyl, 4-alkoxycarbonyl, 2-trifluoromethyl, 3-trifluoromethyl, 4-trifluoromethyl, 2-cyano, 3-cyano, 4-cyano, 2-chloro, 3-chloro, 4-chloro, pentachloro, and pentafluoro.

The term "substituted amine" denotes an amine group which is substituted, for example, with one or more substituents selected from alkyl, alkoxyalkyl, aryl, and alkylaryl.

The term "substituted arylalkoxy" denotes an arylalkoxy group as defined above which is substituted with one or more substituents, for example, substituents selected from 2-nitro, 4-nitro, 2-alkoxycarbonyl, 4-alkoxycarbonyl, 2-trifluoro-methyl, 3-trifluoromethyl, 4-trifluoromethyl, 2-cyano, 3-cyano, 4-cyano, 2-chloro, 3-chloro, 4-chloro, pentachloro, and pentafluoro.

The term "metal" when used alone denotes a metal prone to forming stable alkoxides, such as, for example, lithium, sodium, potassium, magnesium, calcium and the like.

The term "low valent metal" denotes metals, such as, for example, Zn, Li, Na, K and the like, preferably Zn, and amalgams of Zn, such as Zn[Cu], Zn[Ag], Zn[Ag]. Especially preferred is zinc in the presence of chlorotrimethylsilane.

The invention relates to a process for the preparation of a tautomeric mixture of the compounds of the formulas

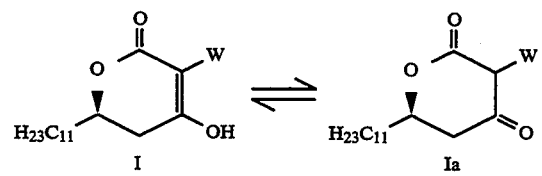

wherein W is hydrogen or $C_6H_{13}$.

More particularly, the process for preparing a tautomeric mixture of compounds of formulas I and Ia comprises treating the compound of the formula

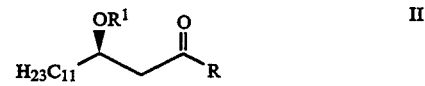

wherein R is unsubstituted or substituted alkoxy, arylalkoxy, aryloxy or amine, $R^1$ is hydrogen or when R is alkoxy, substituted alkoxy, substituted amine, unsubstituted or substituted arylalkoxy $R^1$ can also be metal, with the compound of the formula III

wherein both X and Y are reducible groups or X is hydrogen and Y is a reducible group or Y is hydrogen and X is a reducible group; W is hydrogen or $C_6H_{13}$, and Z is hydroxy or a leaving group, to yield the compound of formula IV

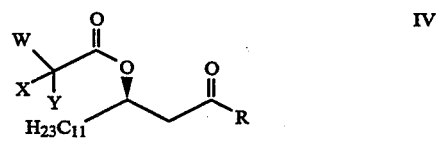

wherein R, X, Y and W are as defined above, which is treated with a low valent metal to form a tautomeric mixture of compounds of formulas I and Ia.

In accordance with the invention, a compound of the formula II wherein R and $R^1$ are as described above, is treated with a compound of the formula III wherein X, Y, W and Z are as described above, to yield a compound of the formula IV wherein R, X, Y, and W are as described above. The reaction is carried out in a conventional aprotic organic solvent, for example, hexane or ether, preferably hexane. When $R^1$ is metal the preferred solvent is tetrahydrofuran. When Z is hydroxy the preferred solvent is methylene chloride. The reaction is preferably carried out in the presence of a base such as, preferably, pyridine, under preferably an inert atmosphere, for example, under nitrogen or the like, at a temperature preferably in the range of from about 0° C. to about 25° C. The compound of formula IV can be purified, for example, by radial chromatography eluting with $CH_2Cl_2$.

The compound of formula IV is converted to a tautomeric mixture of the compounds of formulas I and Ia by reduction of the X or Y substituent whichever contains the reducible group, by treating the compound of formula IV with a low valent metal, for example, Zn, Li, Na, K and the like, preferably Zn, and amalgams of Zn, such as Zn[Cu], Zn[Ag], Zn[Hg]. While any low valent metal may be used it is preferred to use zinc in the presence of chlorotrimethylsilane. The reaction is carried out in a conventional aprotic organic solvent, preferably ether, at preferably reflux temperature. The tautomeric mixture of compounds of the formulas I and Ia is isolated, for example, by extraction with organic solvents, such as ether or ethyl acetate, preferably ether, and purified, for example, by trituration with hexane.

The starting material of formula II wherein $R^1$ is hydrogen, can be prepared by known methods as illustrated below.

When R is alkoxy, substituted alkoxy, substituted amine, the compound of formula II can be prepared by asymmetric hydrogenation of the corresponding β-ketoester, which are known compounds or can be prepared by known methods. For example, the β-keto ester can be prepared by a two step process involving condensation of lauroyl chloride with Meldrum's acid to form the compound of the formula

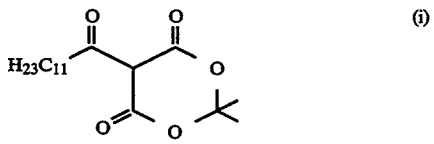
(i)

which can be treated with the desired alcohol or amine.

When R is benzyloxy, aryloxy or substituted aryloxy, the compound of formula II can be prepared by desilylation of a β-silyloxycarboxylic ester of the formula

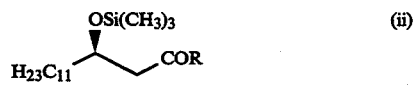
(ii)

which is formed by esterification of β-silyloxy carboxylic acid of the formula

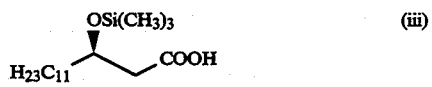
(iii)

prepared by silylation of R-3-hydroxytetradecanoic acid of the formula

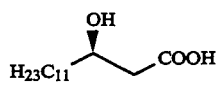
(iv)

The starting materials of formula II wherein $R^1$ is metal are novel and can be prepared by treating a compound of formula

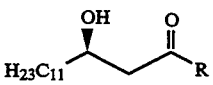
(v)

wherein R is alkoxy, substituted alkoxy, substituted amine, unsubstituted or substituted arylalkoxy, with the appropriate metal hydride in an aprotic organic solvent.

The compounds of formula III are known compounds or can be prepared according to known procedures. See, for example, Pizey, Synthetic Reagents Vol. 1, pgs. 321–357, Wiley, N.Y. (1974); Aizpurua, et al., Reagents and Synthetic Methods; 14. A Facile Synthesis of Carboxylic Acid Bromides and Esters under Neutral Conditions via Reaction of the Trimethylsilyl Esters with Triphenylphosphine Dibromide, Synthesis p. 684 (August 1982).

In a preferred embodiment, in the compound of formula II, R is alkoxy, preferably, methoxy, $R^1$ is hydrogen and in the compound of formula III, X is halogen, preferably, bromine, Y is hydrogen, and Z is halogen, preferably chlorine.

The examples which follow further illustrate the invention.

EXAMPLE 1

Process for the Preparation of 2-Bromooctanoyl Chloride

To a solution of 20 g (90 mmol) 2-bromooctanoic acid in 100 mL toluene was added 13.2 mL (180 mmol) thionyl chloride. The solution was heated at reflux under nitrogen for 3 hours. The excess thionyl chloride and toluene were distilled at atmospheric pressure under $N_2$. The yellow residue was purified by kugelrohr distillation (bp=60°–65° C./0.1 mm Hg) and 13.8 g (64%) of the 2-bromooctanoyl chloride as a colorless oil was isolated.

$^1$H NMR ($CDCl_3$) δ 0.85–0.95 (m, 3H, $CH_3$), 1.24–1.57 (m, 8H, $CH_2$), 1.98–2.22 (m, 2H, $CH_2CBr$) 4.51 (t, J=7.10 Hz, 1H, CHBr); IR ($CHCl_3$) 1788 (C=O) $cm^{-1}$; microanalysis: calcd. for $C_8H_{14}BrClO$- 39.78% C, 5.84% H, 33.08% Br, 14.68% Cl, found- 39.55% C, 5.91% H, 33.17% Br, 14.84% Cl.

EXAMPLE 2

Process for the Preparation of (R)-3-[(2-Bromo-1-Oxooctyl)Oxy] Tetradecanoic Acid Methyl Ester To a rapidly-stirred slurry of 5.18 g (20.0 mmol) methyl (R)-3-hydroxytetradecanoate and 5.03 g (20.8 mmol) 2-bromooctanoyl chloride in 100 mL hexanes at 0° C. in a flame-dried flask under $N_2$ was added 1.67 mL (20.6 mmol) pyridine all at once. After stirring for 10 minutes the cloudy white mixture was poured into a separatory funnel containing a mixture of 200 mL tap $H_2O$/100 mL ether. This mixture was shaken and the layers separated. The aqueous layer was extracted with 2×100 mL ether. The combined ether layers were washed with 200 mL brine, and 3×200 mL H$_2$O. The ether was dried over MgSO$_4$ and removed by rotary evaporation, giving 8.95 g crude product. This yellow oil was dissolved in 30 mL CH$_2$Cl$_2$ and suction filtered through a 1" pad of silica gel 60 in a 60 mL coarse sintered glass funnel, washing with 150 mL CH$_2$Cl$_2$. Rotary evaporation gave 8.10 g (87%) (R)-3-[(2-bromo-1-oxooctyl)oxy]tetradecanoic acid methyl ester as a yellow oil. The oil was found to be suitable for use in the cyclization reaction producing the lactone of Example 5. Analytically pure samples could be prepared by subjecting the oil to radial chromatography, eluting with CH$_2$Cl$_2$.

TLC Analysis

The purified product showed two diastereomers, R$_f$=0.47 and 0.43 (silica gel, CH$_2$Cl$_2$), phosphomolybdic acid visualization). The crude product showed an additional faint spot at R$_f$=0.04, presumably due to starting material.

$^1$H NMR (CDCl$_3$) δ 0.85–0.95 (m, 6H, CH$_3$), 1.20–1.50 (m, 26H, CH$_2$), 1.58–1.72 (m, 2H, CH$_2$), 1.89–2.11 (m, 2H, CH$_2$), 2.53–2.69 (m, 2H, CH$_2$CO), 3.67 (s, 0.43H, Ome of one diastereomer), 3.68 (s, 0.57H, OMe of the other diastereomer), 4.17 (t, J=7.43 Hz, 1H, CHBr), 5.28 (m, 1H, HCO); IR (CHCl$_3$) 1737 (C=O) cm$^{-1}$; MS m/e(rel intensity) 462 (1) (M+), 383 (4), 57 (18), 241 (51); microanalysis: calcd. for C$_{23}$H$_{43}$O$_4$ Br 59.60% C, 9.35% H, 17.24% Br, found 59.66% C, 9.25% H, 17.36% Br.

EXAMPLE 3

(R)-3-[2-Bromo-1-Oxooctyl)Oxy]Tetradecanoic Acid Methyl Ester

The following were added sequentially to 200 mL CH$_2$Cl$_2$ in a flame-dried round bottom flask under N$_2$: 10.0 g (44.8 mmol) 2-bromooctanoic acid, 9.30 g (36.0 mmol)methyl(R)-3-hydroxytetradecanoate, 7.43 g (36.0 mmol)N,N'-dicyclohexycarbodiimide, and 0.508 g (4.16 mmol)4-dimethylaminopyridine. The mixture was stirred for 1 hour, followed by removal of the solvent by rotary evaporation. The resulting oily white solid was stirred with 250 mL hexanes for 5 minutes, followed by suction filtration and washing with 250 mL hexanes. The filtrate was washed with 2×100 mL 1M HCl, 2×100 mL 10% NaHCO$_3$ and 2×100 mL H$_2$O. Drying over MgSO$_4$ and removal of the solvent by rotary evaporation gave a 16.1 g mixture of yellowish oil and white solid particles. This mixture was dissolved in 15 mL 50% CH$_2$Cl$_2$/hexanes and applied to a 2.5 cm×17.5 cm silica gel 60 (70–230 mesh) column, eluting with CH$_2$Cl$_2$/hexanes by means of suction (flow rate=50 mL/min). Isolated was 14.2 g (85% yield based on 2-bromooctanoic acid) (R)-3-[2-bromo-1-oxooctyl)oxy]tetradecanoic acid methyl ester.

EXAMPLE 4

(R)-3-[2-Bromo-1-Oxooctyl)Oxy]Tetradecanoic Acid Methyl Ester 98 mg (3.3 mmol) Sodium hydride (80% in mineral oil) was added to a solution of 764 mg (2.96 mmol) methyl(R)-3-hydroxytetradecanoate in 20.0 mL tetrahydrofuran. After 25 minutes, a solution of 732 mg (3.03 mmol) 2-bromooctanoyl chloride in 10.0 mL tetrahydrofuran was added dropwise via syringe to the cloudy off-white mixture. After 10 minutes at 0° C., the reaction flask was removed from the cold bath for 24 hours. The mixture was poured into 100 mL 10% NaHCO$_3$ and extraction with ether (3×50 mL) was performed. Drying over MgSO$_4$ and removal of the solvent by rotary evaporation gave yellow oil. Purification by flash chromatography (3×24 cm column, 50% CH$_2$Cl$_2$/hexane) gave 407 mg (30% yield based on methyl (R)-3-hydroxytetradecanoate) (R)-3-[2-bromo-1-oxooctyl)oxy]tetradecanoic acid methyl ester.

EXAMPLE 5

Process for the Preparation of (R)-3-Hexyl-5,6-Dihydro-4-Hydroxy-6-Undecyl-2H-Pyran-2-One In a flame-dried flask under N$_2$ a mixture of 744 mg (11.4 mmol) zinc and 1.03 g (2.22 mmol) bromodiester from example 2 in 10 mL 20% v:v Et$_2$O in chlorotrimethylsilane was heated at reflux with rapid stirring for 20 minutes. The mixture was cooled to room temperature and suction filtered through a coarse fritted funnel, using a pad of celite, and washing with 10 mL Et$_2$O. The homogeneous filtrate was cooled in an ice/H$_2$O bath and 10 mL tap H$_2$O was added with stirring. After 10 minutes, the mixture was poured into 100 mL tap H$_2$O and extraction with 3×50 mL Et$_2$O was performed. The combined organic layers were washed with 50 mL brine and dried over MgSO$_4$. The Et$_2$O was removed by rotary evaporation giving 773 mg crude white solid. The solid was slurried in 15 mL hexanes for 30 minutes, followed by suction filtration through a medium fritted funnel and washing with 6.5 mL hexanes. The product was dried under 25" vacuum at room temperature for 1 h, giving 478 mg (61%) (R)-3-hexyl-5,6-dihydro-4-hydroxy-6-undecyl-2H-pyran-2-one as a white waxy powder, mp=110°–112° C.

TLC Analysis

R$_f$=0.26 (20% EtOAc/hexanes) and 0.40 (CH$_2$Cl$_2$) (silica gel, UV and phosphomolybdic acid visualization).

Spectra $^1$H NMR (CDCl$_3$-in solution, the compound was a mixture of keto and enol forms) δ 0.83–0.96 (m, 6H, CH$_3$), 1.19–2.00 (m, 30H, CH$_2$), 2.2–2.8 (m, 2H, pyrone CH$_2$) 3.22 (t, J=5.39 Hz, 0.2H, O=CCHC=O of one isomer), 3.41 (t, J=5.39 Hz, 0.6H, O=CCHC=O of the other isomer), 4.28–4.37 (m, 0.2H, O—CH of enol form), 4.52–4.60 (m, 0.2H, O—CH of one isomer of keto form), 4.64–4.72 (m, 0.6H, O—CH of other isomer of keto form), 6.45 (br s, 0.2H, OH); IR (KBr) 2660 (OH), 1595 (ester C=O), 1380 (C=C) cm$^{-1}$; MS m/e (rel intensity) 352 (1) (M+) 269 (47), 209 (25), 153 (41).

Microanalysis

Calcd. for C$_{22}$H$_{40}$O$_3$—74.95% C, 11.44% H, found—75.18% C, 11.62% H [α]$^{20}$D= −44.69° (1% in dioxane).

EXAMPLE 6

Process for the Preparation of (R)-3-t-butyldimethylsilyloxytetradecanoic Acid A mixture of 2.44 g (R)-3-hydroxytetradecanoic acid (0.01 mole), 2.72 g imidazole (0.04 mole), 3.03 g t-butyldimethylsilyl chloride (0.02 mole), and 50 mL dichloromethane was stirred at room temperature for 22 hours. 5 mL Methanol was added and the resultant mixture was stirred at room temperature for 15 minutes after which it was concentrated to dryness on a rotary evaporator (ca. 100 mm Hg, 35° C.). The residue was chromatographed on a 1" column slurry packed with silica gel in chloroform. The product was eluted with 5% methanol in chloroform. The chromatography was monitored by TLC (silica gel, 5% methanol in chloroform, phosphomolybdic acid visualization, product Rf ca. 0.6) and fractions containing only product were pooled and concentrated on a rotary evaporator (ca. 1 mm Hg, 30° C.) to a clear oil (2.84 g, 79% yield).

$^1$HNMR (CDCl$_3$) δ 0.078 (m, 6H), 0.88 (m, 12H), 1.26 (m, 18H), 1.52 (m, 2H), 2.50 (m, 2H), 4.10 (m, 1H), acid proton broad, ca. δ 11.

HR-MS: calculated; 359.2982 (M+1). found: 359.2981.

EXAMPLE 7

Process for the Preparation of Phenyl(R)-3-t-Butyl-Dimethylsilyloxytetradecanoate A solution of 2.71 g (R)-3-t-butyldimethylsiloloxytetradecanoic acid (0.0076 moles) in 20 mL dichloromethane was cooled with stirring to 5° C. 0.72 g Phenol (0.0076 moles), then 1.72 g N,N'-dicyclohexylcarbodiimide (0.0084 moles) were added and the resultant mixture was allowed to warm to room temperature and stirred there for about 16 hours. The mixture was filtered through a coarse sintered glass funnel, and the collected solids were washed with about 5 mL dichloromethane. The combined filtrate and washes were concentrated to dryness on a rotary evaporator (about 100 mm Hg, 30° C.). The residue was chromatographed on a 2" column slurry packed with silica gel (about 150 g) in dichloro-methane. The product was eluted with dichloromethane. The chromatography was monitored by TLC (silica gel, dichloromethane, phosphomolybdic acid visualization, product Rf ca 0.95). Fractions containing only product were pooled and concentrated to an oil on a rotary evaporator (ca. 125 mm Hg, 30° C.). The oil was blown dry by passing a stream of nitrogen over it for 1 hour. A clear oil (2.71 g, 82% yield) was obtained.

$^1$HNMR (CDCl$_3$) δ 0.084 (m, 6H), 0.89 (m, 12H), 1.20–1.40 (m, 18H), 1.56 (m, 2H), 2.68 (m, 2H), 4.24 (m, 1H), 7.08 (m, 2H), 7.23 (m, 1H), 7.37 (m, 2H)

HR-MS: calculated; 435.3294 (M+1); found: 435.3304.

EXAMPLE 8

Process for the Preparation of Phenyl(R)-3-Hydroxytetradecanote

A solution of 5.80 g phenyl(R)-3-t-butyl-dimethylsilyloxytetradecanoate (13.34 mmol), 54 mL tetrahydrofuran, 6 mL acetic acid, and 25.26 g tetrabutylammonium fluoride trihydrate (80 mmol) was allowed to stir at room temperature for 22.5 hours. The solution was concentrated on a rotary evaporator (ca. 100 mm Hg, 30° C.). To the residue was added 70 mL ethyl acetate. It was then placed into a separatory funnel and washed with 100 mL 0.1N hydrochloric acid, then 100 mL saturated sodium bicarbonate, then 100 mL saturated sodium chloride and finally dried over magnesium sulfate. The mixture was then gravity filtered and concentrated on a rotary evaporator (ca. 100 mm Hg, 30° C.). The residue was chromatographed on a 2' by 1.5" column packed with silica gel (200 g) in hexanes. Fractions containing only product were combined and concentrated on a rotary evaporator (ca 100 mm Hg, 30° C.). A white powder (1.02 g, 24% yield) was obtained.

$^1$H NMR (CDCl$_3$) δ 0.89 (t, 3H), 1.27 (m, 16H), 1.55 (m, 4H), 2.71 (m, 3H), 4.12 (m, 1H), 7.09 (d, 2H), 7.26 (m, 1H), 7.39 (t, 3H).

EXAMPLE 9

Process for the Preparation of Phenyl-(R)-3-(2-Bromo-1-Oxooctyloxy)Tetradecanoate A mixture of 1.02 g phenyl-(R)-3-hydroxytetradecanoate (3.19 mmol), 22 mL dichloromethane, 0.74 g 2-bromooctanoic acid (3.19 mmol), 0.66 g N,N'-dicyclohexylcarbodiimide (3.20 mmol) and 0.39 g 4-dimethylaminopyridine (3.19 mmol) was stirred at room temperature for 1.5 hours. The solution was then concentrated to dryness on a rotary evaporator (ca. 26 mm Hg, 30° C.). 25 mL hexanes was added to the white powdery residue and the resultant mixture was stirred at room temperature for 5 minutes. The slurry was filtered through a coarse sintered glass funnel and the solids were washed with 2×20 mL hexanes. The combined filtrates were placed in a separatory funnel and washed with 2×50 mL 1M HCL, 2×50 mL 10% saturated sodium bicarbonate and 2×50 mL city water. The organic layer was dryed over magnesium sulfate, then gravity filtered through paper, and concentrated on a rotary evaporator (ca. 10 mm Hg, 30° C.). The residue was chromatographed on a 2' by 1" column slurry packed with silica gel (80 g) in hexanes. Product was eluted with 50/50 hexanes and dichloromethane. The chromatography was monitored by TLC (silica gel, 50/50 hexanes: dichloromethane, phosphomolybidic acid visualization). Fractions containing only product were pooled and concentrated on a rotary evaporator (ca. 100 mm Hg, 30° C.). A cloudy oil (0.98 g, 58% yield) was obtained.

$^1$H NMR (CDCl$_3$) δ 0.88 (m, 3H), 1.26 (m, 26H), 1.40 (m, 2H), 1.74 (m, 2H), 1.97 (m, 1H), 2.03 (m, 1H), 2.84 (m, 2H), 4.20 (m, 1H), 5.41 (m, 1H), 7.09 (m, 2H), 7.23 (m, 1H), 7.37 (t, 2H).

EXAMPLE 10

Process for the Preparation of (R)-3-Hexyl-5,6-Dihydro-4-Hydroxy-6-Undecyl-2H-Pyran-2-One In a flame-dried flask under N$_2$ a mixture of 336 mg (5.14 mmol) zinc and 510 mg (0.99 mmol) (R)-3-[(2-bromo-1-oxoocty)oxy]tetradecanoic acid phenyl ester in 5.0 ml 20% v:v Et$_2$O:chlorotrimethylsilane was heated at reflux with rapid stirring for 20 minutes. The mixture was cooled to room temperature and suction filtered through a coarse fritted funnel, using a pad of celite, and washing with 5 ml Et$_2$O. The homogenous filtrate was cooled in an ice/H$_2$O bath and 5 ml tap H$_2$O was added with stirring. After 10 min, the mixture was poured into 50 ml tap H$_2$O and extraction with 3×25 ml Et$_2$O was performed. The combined organic layers were washed with 25 ml brine and dried over MgSO$_4$. The Et$_2$O was removed by rotary evaporation, giving a white solid. The solid was stirred with 6.0 ml hexanes for 30 min, followed by suction filtration through a medium fritted funnel. The product was washed with 2.0 ml hexanes and dried under 26" vacuum at room temperature for 1.5 h, giving 235 mg (67%) (R)-3-hexyl-5,6-dihydro-4-hydroxy-6-undecyl-2H-pyran-2-one as a white powder, mp=109°–111° C.; $[\alpha]^{20}D = -43.5°$ (1% in dioxane).

EXAMPLE 11

Process for the Preparation of (R)-3-[(Bromoacetyl)Oxy]Tetradecanoic Acid Methyl Ester To a rapidly-stirred slurry of 1.29 g (4.99 mmol) methyl (R)-3-hydroxytetradecanoate and 0.45 ml (5.2 mmol) bromoacetyl bromide in 25 ml hexanes at 0° C. in a flame-dried flask under $N_2$ was added 0.42 ml (5.2 mmol)pyridine all at once. The mixture was removed from the cold bath for 30 min. The mixture was suction filtered through celite, washing with 75 ml ether. The filtrate was washed with $2 \times 100$ ml $H_2O$ and with 50 ml 10% $NaHCO_3$. The ether was dried over $MgSO_4$ and removed by rotary evaporation, giving 1.70 g (90%) crude (R)-3-[(bromoacetyl)oxy]tetradecanoic acid methyl ester as a yellow oil. Analytically pure samples could be prepared by subjecting the oil to radial chromatography, eluting with $CH_2Cl_2$.

TLC Analysis

The purified product showed one spot, $R_f = 0.40$ (silica gel, $CH_2Cl_2$, phosphomolybdic acid visualization). The crude product showed an additional faint spot at $R_f = 0.11$, presumably due to starting material.

Spectra $^1$H NMR (CDCl$_3$) δ 0.864–0.897 (t, J=6.67 Hz, 3H, CH$_3$), 1.19–1.40 (m, 18H, CH$_2$), 1.58–1.71 (m, 2H, CH$_2$) 2.55–2.68 (m, 2H, CH$_2$—CO$_2$Me), 3.69 (s, 3H, O—CH$_3$), 3.80 (s, 2H, CH$_2$—Br), 5.24–5.31 (m, 1H, CH—O); IR(CHCl$_3$) 1744 (C=O) cm$^{-1}$; MS m/e (rel intensity) 347(1) (M+-OMe), 41(100), 55(61), 74(45); high resolution MS: calcd. for C$_{16}$H$_{28}$BrO$_3$(M+-OMe)—347.1222, found —347.1225.

Microanalysis $[\alpha]^{20}D = 0°$ (1% in CHCl$_3$)

EXAMPLE 12

Process For The Preparation of (R)-5,6-dihydro-4-hydroxy-6-undecyl-2H-pyran-2one In a flame-dried flask under $N_2$ a mixture of 659 mg (10.1 mmol) zinc and 755 mg (1.99 mmol) (R)-3-[(bromoacetyl)oxy]tetradecanoic acid methyl ester in 10 mL 20% v:v Et$_2$O:chlorotrimethylsilane was heated at reflux with rapid stirring for 20 min. The mixture was cooled to room temperature and suction filtered through a coarse fritted funnel, using a pad of celite, and washing with 10 mL Et$_2$O. The homogenous filtrate was cooled in an ice/H$_2$O bath and 10 mL tap H$_2$O was added with stirring. After 10 min, the mixture was poured into 100 mL tap H$_2$O and extraction with $3 \times 50$ mL Et$_2$O was performed. The combined organic layers were washed with 50 mL brine and dried over MgSO$_4$. The Et$_2$O was removed by rotary evaporation giving 669 mg crude yellow solid. The solid was slurried in 9.0 mL hexanes for 30 min, followed by suction filtration through a medium fritted funnel. The product was dried under 25" vacuum at room temperature for 1.5 h, giving 120 mg (22%) (R)-5,6-dihydro-4-hydroxy-6-undecyl-2H-pyran-2-one as a white powder, mp=86°-7° C.

TLC Analysis $R_f=0.05$ (20% EtOAc/hexanes) and 0.17 (5% EtOAc/CH$_2$Cl$_2$) (silica gel, UV and phosphomolybdic acid visualization).

Spectra $^1$HNMR (CHCl$_3$-in solution, the compound was predominantly in the keto form) δ 0.87–0.90 (t, J=6.20 Hz, 3H, CH$_3$), 1.19–1.90 (m, 20H, CH$_2$), 2.47 (dd, J=11.53, 18.32 Hz, 1H, axial O—CH—CH—C=O) 2.71 (d, J=18.32 Hz, 1H, equatorial O—CH—CH—C=O), 3.44 (d, J=18.97 Hz, 1H, O=CCHC=O), 3.58 (d, J=18.97 Hz, 1H, O=CCHC=O), 4.63 (br s, 1H, O—CH—CH—C=O); IR (KBr) 2660 (OH), 1692 (ester C=O), 1585 (ketone C=O) cm$^{-1}$; MS m/e (rel intensity) 268 (1) (M+), 43 (100), 55 (69), 71 (47).

Microanalysis

Calcd. for C$_{16}$H$_{28}$O$_3$-71.60% C, 10.51% H, found-71.49% C, 10.46% H $[\alpha]^{20}D = -43.07°$ (0.98% in dioxane)

We claim:

1. A process for the preparation of a tautomeric mixture of compounds of the formulas

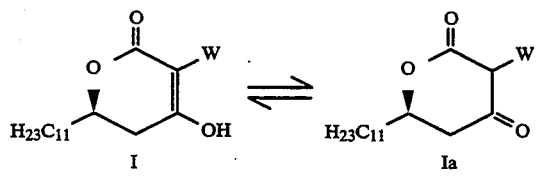

wherein W is hydrogen or C$_6$H$_{13}$, which comprises treating a compound of the formula

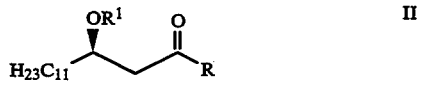

wherein, when R is
  unsubstituted or substituted alkoxy bearing one or more substituents selected from alkoxy, alkoxyalkoxy, dialkylaminoalkoxy, fluorine, and aryl,
  or unsubstituted or substituted arylalkoxy bearing one or more substituents selected from 2-nitro, 4-nitro, 2-alkoxycarbonyl, 4-alkoxycarbonyl, 2-trifluoromethyl, 3-trifluoromethyl, 4-trifluoromethyl, 2-cyano, 3-cyano, 4-cyano, 2-chloro, 3-chloro, 4-chloro, pentachloro and pentafluoro,
  or unsubstituted or substituted aryloxy bearing one or more substituents selected from 2-nitro, 4-nitro, 2-alkoxycarbonyl, 4-alkoxycarbonyl, 2-trifluoromethyl, 3-trifluoromethyl, 4-trifluoromethyl, 2-cyano, 3-cyano, 4-cyano, 2-chloro, 3-chloro, 4-chloro, pentachloro and pentafluoro,
  or unsubstituted or substituted amine bearing one or more substituents selected from alkyl, alkoxyalkyl, aryl and alkylaryl,
R$^1$ is hydrogen or when R is
  unsubstituted or substituted alkoxy bearing one or more substituents selected from alkoxy, alkoxyalkoxy, dialkylaminoalkoxy, fluorine, and aryl,
  or substituted amine bearing one or more substituents selected from alkyl, alkoxyalkyl, aryl, and alkylaryl, or unsubstituted or substituted arylalkoxy bearing one or more substituents selected from 2-nitro, 4-nitro, 2-alkoxycarbonyl, 4-alkoxycarbonyl, 2-trifluoromethyl, 3-trifluoromethyl, 4-trifluoromethyl, 2-cyano, 3-cyano, 4-cyano, 2-chloro, 3-chloro, 4-chloro, pentachloro and pentafluoro, R$^1$ can also be a metal selected from lithium, sodium, potassium, magnesium and calcium with a compound of the formula

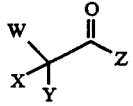

wherein W is defined above, and both X and Y are halogen, alkylsulfide, arylsulfide, alkylselenide or arylselenide or X is hydrogen and Y is halogen, alkysulfide, arylsulfide, alkylselenide or arylselenide or Y is hydrogen and X is halogen, alkylsulfide, arylsulfide, alkylselenide or arylselenide and Z is hydroxy or a leaving group, in an aprotic organic solvent to yield a compound of the formula

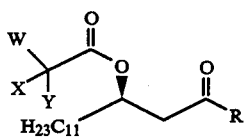

and treating a compound of formula IV with a low valent metal in an aprotic organic solvent to yield the tautomeric mixture of compounds of formulas I and Ia, and if desired, recovering the tautomeric mixture of formulas I and Ia.

2. The process of claim 1, wherein R is alkoxy.
3. The process of claim 2, wherein R is methoxy.
4. The process of claim 2, wherein R$^1$ is hydrogen.
5. The process of claim 1, wherein X is halogen, alkyl sulfide, aryl sulfide, alkyl selenide or aryl selenide; Y is hydrogen, and Z is hydroxy, halogen, unsubstituted or substituted alkoxy, aryloxy, acyloxy, alkoxycarbonyloxy or amino carbonyloxy.
6. The process of claim 1, wherein X is hydrogen, Y is halogen, alkyl sulfide, aryl sulfide, alkyl selenide or aryl selenide and Z is hydroxy, halogen, unsubstituted or substituted alkoxy, other than tert butyloxy and tert amyloxy aryloxy, acyloxy, alkoxycarbonyloxy or aminocarbonyloxy.
7. The process of claim 5, wherein X and Z are halogen.
8. The process of claim 7, wherein X is bromine and Z is chlorine.
9. The process of claim 6, wherein Y and Z are halogen.
10. The process of claim 9, wherein Y is bromine and Z is chlorine.
11. The process of claim 1, wherein the low valent metal is zinc, lithium, sodium, potassium, zinc copper, zinc silver or zinc mercury.
12. The process of claim 11, wherein the low valent metal is zinc in chlorotrimethylsilane.
13. The process of claim 4, wherein the aprotic organic solvent in which the compound of formula II is treated with the compound of formula III is hexane and the aprotic organic solvent in which the compound of formula IV is treated with a low valent metal is ether.

14. The process of claim 1, wherein X is bromine and Y is hydrogen.

15. A process for the preparation of a tautomeric mixture of compounds of the formulas

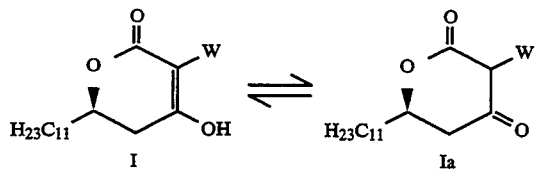

wherein W is hydrogen or C$_6$H$_{13}$, which comprises treating a compound of the formula

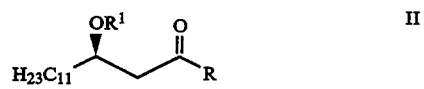

wherein, when R is
unsubstituted or substituted alkoxy bearing one or more substituents selected from alkoxy, alkoxyalkoxy, dialkylaminoalkoxy, fluorine, and aryl,
or unsubstituted or substituted arylalkoxy bearing one or more substituents selected from 2-nitro, 4-nitro, 2-alkoxycarbonyl, 4-alkoxycarbonyl, 2-trifluoromethyl, 3-trifluoromethyl, 4-trifluoromethyl, 2-cyano, 3-cyano, 4-cyano, 2-chloro, 3-chloro, 4-chloro, pentachloro and pentafluoro,
or unsubstituted or substituted aryloxy bearing one or more substituents selected from 2-nitro, 4-nitro, 2-alkoxycarbonyl, 4-alkoxycarbonyl, 2-trifluoromethyl, 3-trifluoromethyl, 4-trifluoromethyl, 2-cyano, 3-cyano, 4-cyano, 2-chloro, 3-chloro, 4-chloro, pentachloro and pentafluoro,
or unsubstituted or substituted amine bearing one or more substituents selected from alkyl, alkoxyalkyl, aryl and alkylaryl, R$^1$ is hydrogen or when R is
unsubstituted or substituted alkoxy bearing one or more substituents selected from alkoxy, alkoxyalkoxy, dialkylaminoalkoxy, fluorine, and aryl,
or substituted amine bearing one or more substituents selected from alkyl, alkoxyalkyl, aryl, and alkylaryl,
or unsubstituted or substituted arylalkoxy bearing one or more substituents selected from 2-nitro, 4-nitro, 2-alkoxycarbonyl, 4-alkoxycarbonyl, 2-trifluoromethyl, 3-trifluoromethyl, 4-trifluoromethyl, 2-cyano, 3-cyano, 4-cyano, 2-chloro, 3-chloro, 4-chloro, pentachloro and pentafluoro, R$^1$ can also be a metal selected from lithium, sodium, potassium, magnesium and calcium with a compound of the formula

wherein W is defined above and both X and Y are bromine or X is hydrogen and Y is bromine or Y is hydrogen and X is bromine and Z is hydroxy, halogen, unsubstituted or substituted alkoxy, other than tert butyloxy and tert amyloxy, aryloxy, acyloxy, alkoxycarbonyloxy or aminocarbonyloxy, in an aprotic organic solvent to yield a compound of the formula

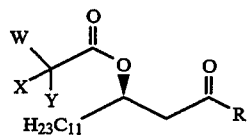

and treating a compound of formula IV with zinc in chlorotrimethylsilane in an aprotic organic solvent to yield the tautomeric mixture of compounds of formulas I and Ia, and if desired, recovering the tautomeric mixture of formulas I and Ia.

16. The process of claim 15, wherein Z is chlorine.

* * * * *